United States Patent [19]

Raina et al.

[11] Patent Number: 5,032,576

[45] Date of Patent: Jul. 16, 1991

[54] METHOD FOR CONTROLLING FEMALE MOTHS USING A PEPTIDE

[75] Inventors: Ashok K. Raina, Beltsville; Howard Jaffe, Gaithersburg; Thomas G. Kempe, Bowie, all of Md.

[73] Assignee: The United States of America as represented by the Secretary of Agriculture, Washington, D.C.

[21] Appl. No.: 354,326

[22] Filed: May 19, 1989

[51] Int. Cl.[5] .............................................. A61K 37/02
[52] U.S. Cl. .................................... 514/12; 530/324; 530/858; 530/855; 514/2
[58] Field of Search ............... 330/324, 325, 350, 858; 514/12, 13, 21, 2

[56] References Cited

PUBLICATIONS

Biochem. and Biophys. Res. Com., vol. 135, No. 2, (1986) pp. 622–628, Jaffa et al.
Chem. Abs. 108 (21), 182947t, (1988), Matsumoto et al.
Chem. Abs. 105(17), 150065a, (1986) Matsumoto et al.
A. K. Raina & J. A. Klun, "Brain Factor Control of Sex Pheromone Production in the Female Corn Earworm Moth," Science 225: 531–533 (1984).
H. Jaffe et al., "HPLC Isolation and Purification of Pheromone Biosynthesis Activating Neuropeptide of Heliothis zea," In Insect Neurochemistry and Neurophysiology, A.B. Borkovec and D. B. Genman, eds., pp. 219–224, Humana Press, Clifton, N.J. (1986).
A. K. Raina et al., "Characteristics of a Neurohorone That Controls Sex Pheromone Production in Heliothis zea," J. Insect Physiol. 33: 809–814 (1987).
H. Nagasawa et al., "Isolation of Pheromone Biosynthesis Activating Neuropeptide of the Silkworm, Bombyx mori," Agric. Biol. Chem. 52: 2985–2987 (1988).

Primary Examiner—John Doll
Assistant Examiner—T. D. Wessendorf
Attorney, Agent, or Firm—David R. Sadowski; M. Howard Silverstein

[57] ABSTRACT

A pheromone biosynthesis activating neuropeptide (Hez-PBAN) hormone, controlling sex pheromone production in moths and controlling melanizing in larvae, was isolated from the brain-suboesophageal ganglion complexes of adult corn earworm *Heliothis zea*. Hez-PBAN has 33 amino acide residues and a molecular weight of 3900; its amino acid sequence is unique among the fully characterized peptide hormones. Synthetic PBAN and related structures induced production of sex pheromone in ligated *H. zea* females and other moth species and melanization in larvae that resulted in morphological changes or death.

5 Claims, No Drawings

METHOD FOR CONTROLLING FEMALE MOTHS USING A PEPTIDE

BACKGROUND OF THE INVENTION

1. Field of the Invention

This invention relates to polypeptide hormones which cause species of moths to produce and release sex pheromones and melanization (black coloration) in the larvae or both. These new polypeptides will be useful in the control of insect pests and the study of insect physiology.

2. Abbreviations

Abbreviations used in the application are as follows: Ala=L-alanyl; Arg=L-arginyl; Asn=L-asparaginyl; Asp=L-aspartyl; Boc=tert-butyloxycarbonyl; Bzl=benzyl; CM=carboxymethyl; Cl-Z=O-chlorobenzyloxycarbonyl; $Cl_2Bzl$=2,6-dichlorobenzyl; DCC=dicyclohexylcarbodiimide; DIEA=diisopropylethylamine; DMF=N,N-dimethylformamide; Gln=L-glutiminyl; Glu=L-glutamyl; Hez-PBAN=pheromone biosynthesis activating neuropeptide of Heliothis zea; HOBt=N-hydroxybenztriazole; HPLC=high performance liquid chromatography; Ile=L-isoleucyl; Leu=L-leucyl; Lys=L-lysyl; Met=L-methionyl; Met(SO)=methionyl sulfoxide; OcHex=O-cyclohexyl-ester; Phe=L-phenylalanyl; Pro=L-prolyl; Ser=L-seryl; TFA=trifluoroacetic acid; Thr=L-threonyl; Tos=tosyl; Tyr=L-tyrosonyl.

3. Summary of the Prior Art

Moths produce and release sex pheromones to attract conspecific males for mating. In the corn earworm, Heliothis zea, and several other species of moths, pheromone production exhibits a diel periodicity [Raina et al., Ann. Entomol. Soc. Am. 79: 128 (1986)]. Sex pheromone production in H. zea was shown to be controlled by a brain factor [Raina and Klun, Science 225: 531 (1984)]. Subsequently it was reported that the factor is a peptide hormone produced in the suboesophageal ganglion of both males and females, and released via the corpora cardiaca into the hemolymph at the onset of scotophase to induce pheromone biosynthesis [Raina et al., J. Insect Physiol. 33: 809 (1987)]. A simple and highly sensitive bioassay was also developed for the hormone designated Hez-PBAN [Raina and Klun, supra (1984)].

SUMMARY OF THE INVENTION

It is an object of this invention to describe the isolation and characterization of the pheromone biosynthesis activating neuropeptide from H. zea (Hez-PBAN).

Another object of this invention is to teach methods of synthesis of Hez-PBAN and structurally related polypeptides.

A further object of the invention is to provide methods of insect control by the use of Hez-PBAN and structurally related polypeptides.

Other objects and advantages of this invention will become readily apparent from the ensuing description.

DETAILED DESCRIPTION OF THE INVENTION

It has been discovered that compounds of the Formula I:

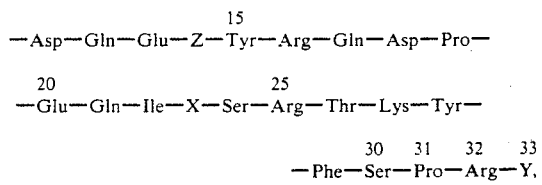

where X is Asp or Asn, Y is Leu or Leu($NH_2$), and Z is Met or Met(SO), have biological activity in insects, stimulating biosynthesis of sex pheromone in female moths or having melanization properties in larvae which may result in morphological changes or death, or both, during development.

Preferred are compounds of the Formula I wherein X is Asn, Y is Leu, and Z is Met.

Particularly preferred are compounds of the Formula I wherein X is Asn, Y is Leu($NH_2$), and Z is Met.

Most particularly preferred are compounds of the Formula I wherein X is Asp, Y is Leu($NH_2$), and Z is Met.

Also included in this invention are precursor peptides of Formula I wherein the peptide sequence starts with Met, used as initiation codon for transcription of genetically engineered hormone, and a C-terminal containing a Gly moiety to allow for glycine-directed amidation through enzymatic conversion to give a C-terminal Leu($NH_2$) as appears in the naturally occurring PBAN.

The nomenclature used to define the peptide is that specified by Schroder and Lubke ["The Peptides," Academic Press (1965)] wherein, in accordance with conventional representation, the N-terminal appears to the left and the C-terminal to the right. Where the amino acid residue has isomeric forms, it is the L-form of the amino acid that is represented herein unless otherwise expressly indicated.

The compound of Formula I wherein X is Asp, Y is Leu($NH_2$), and Z is Met(SO) was isolated from about 5,000 brain-suboesophageal ganglion complexes dissected from male and female Heliothis zea adults using combinations of high performance liquid chromatography and size-exclusion chromatography. A highly purified fraction was used for the determination of amino acid composition and bioassays.

Hez-PBAN was isolated from two sets of ca. 2,500 brain-suboesophageal ganglion complexes dissected from male and female H. zea adults. We used the three-step isolation procedure (Example 1) that was a modification of a previously reported method used for the purification of this peptide [Jaffe et al., In "Insect Neurochemistry and Neurophysiology," A. B. Borkovec and D. B. Gelman (eds.), Humana Press, New Jersey, pp. 219–224 (1986)]. Fractions from high performance liquid chromatography (HPLC) with Supelcosil LC-column (step I) showed biological activity in three distinct fractions eluting at 44–45, 49, and 51 min [Raina et al., In "Insect Neurochemistry and Neurophysiology," A. B. Borkovec and D. B. Gelman (eds.), Human Press, New Jersey, pp. 215–218 (1986)]. Most activity was associated with the 44–45 min fractions, and these were purified further. Step II used four I-125 Protein Pak high performance size exclusion columns. Biological activity was found in fractions eluting at 33–34 min. These were pooled and rerun on a Vydac C-18 column (Step III) to yield a single biologically active peak eluting at 20.5 min. Amino acid analysis of ca. 25 pmoles of the peptide by using an Applied Biosystems Model 420A derivatizer/analyzer revealed the following composition: Asx 5.2 (5), Glx 4.5 (5), Ser 2.2 (2), Gly 2.6 (0), Arg 2.7 (3), Thr 1.6 (2), Ala 2.2 (2), Pro 3.5 (4), Tyr 1.7 (2), Met 1.0 (2), Ile 0.8 (1), Leu 1.6 (2), Phe 0.8 (1), and Lys 0.9 (1) (values in parentheses indicate the number of residues found in complete sequence). Determination of the amino acid sequence was first carried out with ca. 50 pmoles purified peptide by using an Applied Biosystems Model 470A gas phase sequencer. A second analysis performed with ca. 200 pmoles of the peptide by using an Applied Biosystems Model 477A pulsed liquid phase sequencer on line with a Model 120A phenylthiohydantion (PTH) analyzer. Data obtained from 33 cycles indicated the following sequence: Leu-Ser-Asp-Asp-Met-Pro-Ala-Thr-Pro-Ala-Asp-Gln-Glu-Met-Tyr-Arg-Gln-Asp-Pro-Glu-Gln-Ile-?-Ser-Arg-Thr-Lys-Tyr-Phe-Ser-Pro-?-Leu. The residues at positions 23 and 32 were not determined. A third analysis with the same instrument confirmed the earlier sequence and established the presence of Asp and Arg at positions 23 and 32, respectively. The amino acid composition was in good agreement with sequence data, except for extraneous glycine and low methionine. The low yield of methionine commonly results from oxidation, whereas the glycine was apparently an artifact of isolation protocols. Carboxyl terminal sequencing revealed that Leu was the C-terminus, as was evident by its complete release at the two-minute time point. The next residue released was Arg, followed by Pro, Ser, Phe, Tyr, and Lys, which confirmed the sequence data for the last seven residues.

The mass spectra of the peptide were obtained on a Californium-252 time of flight plasma desorption mass spectrometer. Two peaks were observed, each containing about 100 ions in its central channel. The first $(M+H)^+$ was at m/z 3934, and the second, broader peak was the $(M+2H)^{++}$ ion at m/z 1966 corresponding to an $(M+H)^+$ of 3931.

Three 33-amino acid peptides were synthesized by solid phase synthesis, wherein position 23 was Asp or Asn and position 33 was Leu or Leu(NH$_2$). Final purification of the peptides was carried out by HPLC (same as step III in isolation). Their UV spectra were similar to but not identical with the native peptide. It was noted from the literature that oxidation of methionine to methionine sulfoxide occurs during the isolation of peptides and proteins from natural sources [Vale et al., Science 213: 1394 (1981); Houghton and Li, Methods Enzymol. 91: 549 (1983)]. Consequently, when the synthetic peptides were oxidized (see Example 8), the oxidized C-terminal amide having Asp at position 23 closely matched in the retention time and UV spectrum with the native peptide. The calculated mass for the native peptide $(M+H)$ ion using the most abundant ion in the isotope cluster was 3899. Addition of two oxygens, one for each methionine, gave 3931, in good agreement with the experimental value of 3931-4. The synthetic unoxidized peptide showed a broad $(M+H)^+$ at m/z 3900 and a $(M+2H)^{++}$ at m/z 1950. On the basis of the above evidence, the following structure was determined for Hez-PBAN: Leu-Ser-Asp-Asp-Met-Pro-Ala-Thr-Pro-Ala-Asp-Gln-Glu-Met-Tyr-Arg-Gln-Asp-Pro-Glu-Gln-Ile-Asp-Ser-Arg-Thr-Lys-Tyr-Phe-Ser-Pro-Arg-Leu-NH$_2$.

As shown above, Hez-PBAN may be obtained by extraction from insects; however, the peptides of this invention may also be synthesized by any suitable method, such as exclusively solid-phase techniques, partial solid-phase techniques, fragment condensation, or classical solution addition. The peptides may also be synthesized by recently developed recombinant DNA techniques which may be used for large-scale use in the field with the purpose of controlling insect reproduction to prevent crop damage.

Synthesis by the use of recombinant DNA techniques, for the purpose of this application, should be understood to include the suitable employment of structural genes coding for the sequence as specified hereinafter.

The synthetic peptides may also be obtained by transforming a microorganism using an expression vector including a promoter or operator, or both, together with such structural genes and causing such transformed microorganisms to express the peptide.

As stated above, the compounds of Formula I may be synthesized by methods well known to those skilled in the art of peptide synthesis, e.g., solution phase synthesis [see Finn and Hoffman, In "Proteins," Vol. 2, 3rd Ed., H. Neurath and R. L. Hill (eds.), Academic Press, New York, pp. 105–253 (1976)], or solid phase synthesis [see Barany and Merrifield, In "The Peptides," Vol. 2, E. Gross and J. Meienhofer (eds.), Academic Press, New York, pp. 3–284 (1979)]. Preferably the synthesis may follow the stepwise solid phase strategy reported by Merrifield [J. Am. Chem. Soc. 85: 2149–2154 (1963)], the teachings of which are incorporated herein by reference.

TABLE I

Amino Acid Derivatives for the Synthesis of a Peptide of the Formula I, with Pheromone Biosynthesis Inducing Activities or Melanizing Effect or Both (Example 1)

| Cycle Number and Amino Acid | Protected Amino Acid | MW | mMol | g | Coupling Procedure |
|---|---|---|---|---|---|
| 33 | Leu—benzhydryl amineresin | | 1 | 2 | |
| 32, 25, 16 | Boc—Arg(Tos) | 442.5 | 4 | 1.77 | C |
| 31, 19, 9, 6 | Boc—Pro | 215.1 | 8 | 1.72 | A |
| | | | 4 | 0.86 | |
| 30, 24, 2 | Boc—Ser(Bzl) | 295.1 | 8 | 2.36 | A |
| | | | 4 | 1.18 | |
| 29 | Boc—Phe | 265.2 | 8 | 2.1 | A |
| | | | 4 | 1.05 | |
| 28, 15 | Boc—Tyr(Cl$_2$Bzl) | 441.2 | 8 | 3.53 | A |
| | | | 4 | 1.76 | |
| 27 | Boc—Lys(Cl—Z) | 314.8 | 8 | 2.5 | A |
| | | | 4 | 1.26 | |
| 26, 8 | Boc—Thr(Bzl) | 309.1 | 8 | 2.48 | A |

TABLE I-continued

Amino Acid Derivatives for the Synthesis of a Peptide of the Formula I, with Pheromone Biosynthesis Inducing Activities or Melanizing Effect or Both (Example 1)

| Cycle Number and Amino Acid | Protected Amino Acid | MW | mMol | g | Coupling Procedure |
|---|---|---|---|---|---|
| | | | 4 | 1.24 | |
| 18, 11, 4, 3 | Boc—Asp(OcHex) | 328.4 | 8 | 2.63 | A |
| | | | 4 | 1.31 | |
| 23 | Boc—Asn | 232.2 | 8 | 0.93 | B |
| 22 | Boc—Ile | 240.2 | 8 | 1.92 | A |
| | | | 4 | 0.96 | |
| 21, 17, 12 | Boc—Gln | 246.3 | 4 | 0.99 | B |
| 20, 13 | Boc—Glu(oBzl) | 337.4 | 8 | 2.70 | A |
| | | | 4 | 1.35 | |
| 14, 5 | Boc—Met | 249.2 | 8 | 1.99 | A |
| | | | 4 | 1.0 | |
| 10, 7 | Boc—Ala | 189.2 | 8 | 1.51 | A |
| | | | 4 | 0.76 | |
| 1 | Boc—Leu | 249.2 | 8 | 2.0 | A |
| | | | 4 | 1.0 | |

The acid labile tert-butyloxycarbonyl (Boc) group may be used for temporary α-N protection, and the more acid stable groups may be used for protection of the side chains of the amino acids. Amino acid derivatives are listed in Table I. Attachment of the peptide chain to a copolymer matrix of styrene and 1% divinylbenzene may employ a benzhydrylamine type handle as reported in Pietta et al. [Chem. Commun., 650-651 (1970)], Hruby et al. [J. Org. Chem. 42: 3552-3556 (1977)], and Tam et al. [Tetrahedron Lett. 22: 2851-2854 (1981)], which teachings are also incorporated by reference. All amino acids may be incorporated following a double coupling protocol with some modifications for particular amino acids. For all reactions except for arginine, asparagine, and glutamine, the first coupling employs the preformed symmetric anhydride method [Hagenmaier and Frank, Hoppe-Seyler's Z. Physiol. Chem. 353: 1973-1976 (1972)] in dichloromethane; the second coupling employs the preformed hydroxybenztriazole ester method [Konig and Geiger, Chem. Ber. 103: 788-798 (1970)] in dimethyl formamide (DMF). For Boc-Arg(Tos), standard DCC coupling conditions are employed to reduce the risk of lactam formation. The second coupling is done with active HOBt ester method in DMF. Boc-Asn and Boc-Gln were exclusively coupled as HOBt esters in DMF to reduce nitrile and amidine formation [Mojsov et al., J. Org. Chem. 45: 555-560 (1980)]. $^{\Sigma}$N-(2-chlorobenzyloxycarbonyl)lysine, Lys(ClZ), is used because it is more stable than the benzyloxycarbonyl derivative to the acid deprotection steps and it also avoids side chain branching [Erikson and Merrifield, J. Am. Chem. Soc. 95: 3757-3763 (1972)]. The β-cyclohexylester (cHex) of Boc-Asp-OH is used; it is also more stable to acids and thus minimizes aspartimide formation [Tam, Tetrahedron Lett., 4033-4036 (1979)]. The quantitative ninhydrin test may be routinely used throughout the synthesis to monitor the extent of coupling after each cycle [Sarin et al., Anal. Biochem. 117: 147-157 (1981)]. Cleavage of the peptides from the resin and removal of all the remaining protecting groups are accomplished by treatment with low-high HF method of cleavage [Tam et al., J. Am. Chem. Soc. 105: 6442-6445 (1983); Yamashiro and Li, J. Am. Chem. Soc. 100: 5174-5179 (1978)]. Crude peptide is removed from the resin by washing with 10% aqueous acetic acid and is then lyophilized and isolated by HPLC.

When the synthetic Hez-PBAN was injected into ligated H. zea females, it caused normal production of the sex pheromone. A dose×response study indicated that there was a linear response between 1.00 and 4.0 pmoles with optimum response obtained between 2.00 and 4.00 pmoles. Table II shows the dose/response data for Hez-PBAN and related peptides. There was a significant decrease in pheromone production at doses greater than 4.0 pmoles. A crude extract of brain-suboesophageal ganglion caused production of pheromones (99.0+17.1 ng, N=9) equivalent to ≃2.5 pmoles of the synthetic peptide. Hez-PBAN, when injected into ligated females of six other species of moths, caused production of significant amounts of their respective pheromones (Table III). In two of the six species, the quantity of pheromone produced was 6-7 times that found in normal females. The expression of pheromonotropic activity of Hez-PBAN in species with different pheromone chemistry suggests that PBAN may be activating an early step in the biosynthetic pathway of these pheromones. The availability of the synthetic peptide will greatly enhance the ability of the researcher to investigate the biochemical processes involved in hormonal control of sex pheromone production in moths. The knowledge thus gained could lead to the development of new methods for the control of insect pests through the interruption of pheromone biosynthesis and reproduction. PBAN when injected into third instar H. zea larvae at 10 pmoles/larva caused intense melanization resulting in black larvae after the moult to the fourth instar. There was also a significant mortality associated with this phenomenon.

The peptides of Formula I stimulate pheromone biosynthesis in adult moths. As a result, these peptides are contemplated as agents for insect control by causing production of pheromone at inappropriate times or in inappropriate amounts, thereby upsetting the normal reproductive cycle.

TABLE II

| Compound Number | X | Y | Z | Dose pMole | ng/Female H. zea (Z)-11-Hexadecenal |
|---|---|---|---|---|---|
| 1 Hex-PBAN | Asp | Leu(NH$_2$) | Met | 1.0 | 4.6 |
| | | | | 10.0 | 128.2 |
| | | | | 100.0 | 179.9 |
| 2 | Asp | Leu(NH$_2$) | Met(SO) | 1.0 | 6.9 |

TABLE II-continued

| Compound Number | X | Y | Z | Dose pMole | ng/Female H. zea (Z)-11-Hexadecenal |
|---|---|---|---|---|---|
| | | | | 10.0 | 108.0 |
| | | | | 100.0 | 136.2 |
| 3 | Asn | Leu(NH$_2$) | Met | 1.0 | 1.7 |
| | | | | 10.0 | 97.1 |
| | | | | 100.0 | 145.7 |
| 4 | Asn | Leu | Met | 10.0 | 0.9 |
| | | | | 100.0 | 3.2 |
| | | | | 1000.0 | 112.1 |

TABLE III

Cross Reactivity of Hex-PBAN in Six Other Species of Moths
Bioassay procedure is described in Example 6. Each female was injected with 5 pmoles of the synthetic peptide in 10 microliter of buffer. The major component in the pheromone of *H. virescens* (tobacco budworm), *S. frugiperda* (fall armyworm), *D. nitidalis* (pickle worm), *O. nubilalis* (European corn borer), *M. sexta* (tobacco hornworm), and *L. dispar* (gypsy moth) are (Z)-11-hexadecenal, (Z)-9-1-ol acetate, (E)-11-hexadecenal, (E)-11-tetradecen-1-ol acetate, (E,Z)-10,12-hexadecadienal, and cis-2-decyl-3-(5-methylhexyl) oxirane, respectively. Sex pheromone titer is expressed in ng of the major component per female ± SE, N = 5.

| | | Quantity of the Major Component in the Pheromone of | | |
|---|---|---|---|---|
| Test Species | Family | Normal Female | Ligated Female | Hex-PBAN injected Female |
| *Heliothis verescens* | Noctuidae | 177.9 ± 21.3 | 5.7 ± 1.6 | 189.2 ± 12.2 |
| *Spodoptera frugiperda* | Noctuidae | 6.9 ± 1.1 | 1.5 ± 0.2 | 42.9 ± 12.2 |
| *Diaphania nitidalis* | Pyralidae | 17.5 ± 5.0 | 2.3 ± 1.0 | 49.2 ± 16.3 |
| *Ostrinia nubilalis* | Pyralidae | 4.0 ± 0.3 | 0.0 | 6.7 ± 1.1 |
| *Manduca sexta* | Sphingidae | 9.0 ± 1.7 | 3.2 ± 0.4 | 65.4 ± 11.9 |
| *Lynmantria dispar* | Lymantriidae | 9.3 ± 2.3 | 0.1 ± 0.06 | 2.5 ± 0.4 |

The peptides or a nontoxic addition thereof, combined with an agriculturally acceptable carrier to form a pesticidal composition, may be administered to larvae, pupae, and/or adult insects either subcutaneously, percutaneously, topically, or orally. The peptides should be at least 90% pure, and preferably should have a purity of at least 98% when administered. However, a purity of as low as about 5% would be substantially greater than the purity of the naturally occurring compound and is considered to have utility in effecting biological responses. This purity means that the intended peptide constitutes the stated weight % of all like peptides and peptide fragments present. Their administration may be employed by an insect virus to stimulate pheromone biosynthesis. The required dosage will vary with the particular condition and with the duration of the desired treatment.

Illustrative of acid addition salts are hydrochloride, hydrobromide, trifluoro acetate, sulphate, phosphate, oxalate, fumarate, gluconate, alginate, maleate, acetate, citrate, benzoate, succinate, malate, ascorbate, tartrate, and the like. Usually the dosage will be from about 1.0 pmole to about 100 pmoles of peptide per insect.

The following examples are intended only to further illustrate the invention and are not intended to limit the scope of the invention which is defined by the claims.

EXAMPLE 1

Isolation of Hez-PBAN

Brain-suboesophageal ganglion complexes from about 2,500 insects were homogenized in 5% formic acid v/v, 15% trifluoroacetic acid (TFA) v/v, 1% NaCl w/v, 1N HCl as described previously [Bennett et al., Analyt. Biochem. 128: 121 (1983)]. The defatted extract was subjected to an HPLC purification procedure based on a sequence of three chromatographic steps (I-III): (I) Supelcosil LC-18 DB with Pelliguard guard column (Supelco) eluted with a concave gradient (Waters Curve 7) of 10-60% acetonitrile containing 0.1% v/v TFA in 0.1% aqueous TFA over 1 hr at ambient temperature and 1.0 mL per min on a Model 840 HPLC with autosampler (Waters). The eluant was monitored at 214 nm. (II) 4x, I-125 HP-SEC columns (Waters) eluted isocratically with a 40% aqueous acetonitrile (0.1% TFA) at ambient temperature and 1.0 mL per min on the same instrument as for (I). (III) Vydac 218 TP 54 C-18 column (Separations Group) eluted with a linear gradient of 10-50% acetonitrile containing 0.1% TFA in 0.1% aqueous TFA, over 1 hr at 28° C. at 0.4 mL per min on a Model 1090M HPLC with photodiode array detector and Chemstation (Hewlett Packard).

EXAMPLE 2

Resin Peptide Synthesis

For exemplification, the following detailed example is directed to the new peptide PBAN having the following structure:

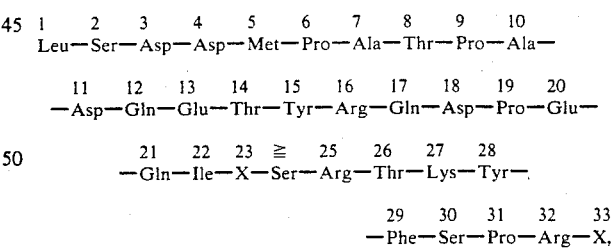

in which X is Asp and Y is Leu(NH$_2$) (see Table I).

As may be seen from the formula above, 33 amino acids are involved; and, in this formula, the positions are numbered according to the accepted procedure beginning at position 1 for Leu on one end of the chain and ending with Leu(NH$_2$) at position 33 at the other end of the chain. For clarity of description, this same numbering system will be followed in referring to the cycles of the synthesis. The assembly of the amino acids begins with cycle 32, which involves the coupling of the amino acid to the Leu moiety, followed by residue 31 and so on to the last amino acid. Protected amino acid derivatives that may be used in the synthesis of the peptide of Formula I are given in Table I. The resin which was functionalized with Leu is available from chemical supply houses. As indicated earlier, three types of coupling procedures are used, depending on the properties of the reactants. In Table I, the amino acid position and cycle number, type of coupling procedure, molecular weights, and amount of reactants for the cycle are given. The details for each coupling protocol A, B, and C are described below.

Double coupling protocol using symmetric anhydride and active ester methods may be used to ensure as complete coupling as possible. The following protocol may be used for all amino acids except for arginine, asparagine, and glutamine. The protocol is given for 2 g benzhydryl type resin functionalized with a total of 1 mMol of leucine.

COUPLING PROCEDURE A

1. The resin is washed with dichloromethane, $CH_2Cl_2$ (30 mL, 6×1 min).
2. Removal of the Boc protecting group is done with 50% TFA in $CH_2Cl_2$ (30 mL, 3×1 min) and with 30 mL for 20 min.
3. The reagent is then removed with $CH_2Cl_2$ wash (30 mL, 6×1 min).
4. Traces of acid are finally removed with 5% DIEA in $CH_2Cl_2$ (30 mL, 2×2 min).
5. A final wash is done before the coupling is completed, $CH_2Cl_2$ (30 mL, 6×1 min).
6. Five milligrams of the resin is removed for ninhydrin test.
7. The protected amino acid (listed in Table I, 8 mMol) dissolved in 10 mL of $CH_2Cl_2$ is then treated with DCC (4 mMol, 825 mg) in 3 mL of $CH_2Cl_2$. After 10 min, the solution is filtered and added to the resin. The precipitate is washed with 10 mL of $CH_2Cl_2$ and added to the reaction vessel, which is then shaken for 2 hr at room temperature.
8. The resin is washed with $CH_2Cl_2$ (30 mL, 4×2 min).
9. The resin is washed with 5% DIEA in $CH_2Cl_2$ (30 mL, 2 min).
10. The resin is washed with $CH_2Cl_2$ (30 mL, 4×2 min).
11. Ninhydrin test is performed.
12. The resin is washed with DMF (30 mL, 2×2 min).
13. HOBt (4 mMol, 540 mg) in 7 mL of DMF at 0° C. is mixed with DCC (4 mMol, 825 mg) in 3 mL of $CH_2Cl_2$. The protected amino acid (listed in Table I, 4 mMol), dissolved in 6 mL of DMF, is then added. The mixture is kept for 10 min at 0° C. and is then added to the resin. The mixture is shaken for 2 hr at room temperature.
14. The resin is then washed with DMF (30 mL, 4×1 min).
15. The resin is washed with $CH_2Cl_2$ (30 mL, 2×2 min).
16. The resin is washed with 5% DIEA in $CH_2Cl_2$ (30 mL, 2 min).
17. The resin is washed with $CH_2Cl_2$ (30 mL, 3×1 min).
18. Ninhydrin test is performed.

COUPLING PROCEDURE B

Coupling procedure B was used for the amino acids asparagine and glutamine:
Steps 1–6 were the same as coupling procedure A.
7. The resin is washed with DMF in $CH_2Cl_2$ (1:2 v/v, 30 mL, 2×2 min).
8. To HOBt (4 mMol, 540 mg) in 7 mL DMF/$CH_2Cl_2$ (1:1 v/v) at 0° C. is added DCC (4 mMol, 825 mg) in 3 mL of $CH_2Cl_2$.

To that mixture is then added the protected amino acid (listed in Table I, 4 mMol) in 6 mL of DMF/$CH_2Cl_2$. The reaction mixture is added to the resin after 10 min at 0° C. The resin is then shaken at 2 hr at room temperature.
9. The resin is washed with DMF/$CH_2Cl_2$ (1:2 v/v, 30 mL, 2×2 min).

The remaining steps in coupling procedure A are then followed.

COUPLING PROCEDURE C

Coupling procedure C was used for the amino acid arginine.
Steps 1–6 were the same as coupling procedure A.
7. The protected amino acid (listed in Table I, 4 mMol) in 10 mL $CH_2Cl_2$ is added to the resin. DCC (4 mMol, 825 mg) in 3 mL $CH_2Cl_2$ is added after 5 min to the resin.

The reaction mixture is then shaken for 2 hr at room temperature.

The steps 8–18 described in coupling procedure A are then followed.

The addition of a Leu represents the completion of the solid phase synthesis. The Boc group is finally removed by steps 1–6 in coupling procedure A. The resin peptides are then removed from the reaction vessel and dried in a vacuum. Cleavage and purification steps are carried out as described below.

EXAMPLE 3

A peptide of Formula I, wherein X is Asn and Y is Leu($NH_2$). The same procedure as described in Example 1 is used, except for the use of Boc-Asn in cycle 23 and coupling procedure B.

EXAMPLE 4

A peptide of Formula I, where X is Asn and Y is Leu. The same procedure as described in Example 3 is used, except for the use of the Boc-Leu Merrifield resin instead of the benzhydrylamine resin.

EXAMPLE 5

Resin Peptide Cleavage

The dried resin peptide (1 g) was premixed with dimethylsulfide, p-thiocresol, and p-cresol; liquid HF at −78° C. was then added to give approximately a final volume of 10 mL (65:2.5:7.5:25 by volume). The mixture was equilibrated to 0° C. by stirring in an ice bath. After 2 hr, the HF and dimethyl sulfide were removed in vacuo. The high HF treatment was initiated by recharging the reaction vessel at −78° C. with about 14 mL of fresh HF to give a total volume of 15 mL HF-p-cresol-p-thiocresol. The reaction was carried out at 0° for 1 hr. After evaporation of HF at 0° C. and washing with cold ether, the crude reaction mixture was extracted with 10% aqueous acetic acid. The mixture was then lyophilized to dryness.

EXAMPLE 6

Purification of Crude Peptides and Biological Activities

The crude peptide was extracted from the resin with aqueous acetic acid (10%) and purified on HPLC (Ultrasphere column, 4.6×250 mm) using a gradient 0–60% acetonitrile (0.01%, trifluoroacetic acid) over 30 min at a flow rate of 1.5 mL per min. The pure peptide eluted at about 18 min and was isolated and characterized using amino acid composition and sequence analysis which confirmed the structure. All peptides were biologically active and stimulated pheromone production.

Dose response of the peptide of Formula I, wherein X is Asp and Y is Leu(NH$_2$): the peptide was dissolved in sucrose phosphate buffer and injected into ligated 3-day-old females during scotophase. Pheromone was extracted 3 hr after injection and quantified by capillary gas chromatography. The dose response study indicated that there was a linear response between 1.0 and 4.0 pmoles. Cross reactivity in other species of moth was observed (see Table III for comparative data).

EXAMPLE 7

Melanizing Assay

Peptide of the Formula I, wherein X is Asp and Y is Leu(NH$_2$) was dissolved in sucrose phosphate buffer and serially diluted to obtain 0.1, 1.0, 10, 100, and 1000 pmoles/5 $\mu$L of buffer. The peptide was then injected into third instar *H. zea* larvae the day before their moult to fourth instar. Observations for melanization (intense black color formation) were recorded after 48 hr. The larvae showed 100% melanization at the 10 pmole dose.

EXAMPLE 8

Preparation of Methionine Sulfoxide Derivatives

The synthetic peptide amide and peptide acid (0.1 mg of each) were dissolved in 200 $\mu$L of 10% aqueous hydrogen peroxide at ambient temperature for 2 hr. The products containing the respective sulfoxides were isolated by HPLC.

Although the invention has been described with regard to its preferred embodiments, which constitute the best mode presently known to the inventors, it should be understood that various changes and modifications as would be obvious to one having the ordinary skill in this art may be made without departing from the scope of the invention, which is set forth in the following claims.

We claim:

1. A method for controlling female moths comprising contacting said moths or larvae of said moths with an effective amount of about 1.0–1000 pmoles of a peptide consisting of the formula Leu-Ser-Asp-Asp-Z-Pro-Ala-Thr-Pro-Ala-Asp-Gln-Glu-Z-Tyr-Arg-Gln-Asp-Pro-Glu-Gln-Ile-X-Ser-Arg-Thr-Lys-Tyr-Phe-Ser-Pro-Arg-Y, where X is Asp or Asn; Y is Leu or Leu(NH$_2$); and Z is Met or Met(SO).

2. A method as described in claim 1 wherein X is Asp; Y is Leu(NH$_2$); and Z is Met.

3. A method as described in claim 1 wherein X is Asp; Y is Leu(NH$_2$); and Z is Met(SO).

4. A method as described in claim 1 wherein X is Asn; Y is Leu(NH$_2$); and Z is Met.

5. A method as described in claim 1 wherein X is Asn; Y is Leu; and Z is Met.

* * * * *

UNITED STATES PATENT AND TRADEMARK OFFICE
CERTIFICATE OF CORRECTION

PATENT NO. : 5,032,576

DATED : July 16, 1991

INVENTOR(S) : Ashok K. Raina; Howard Jaffe; Tomas G. Kempe

It is certified that error appears in the above-indentified patent and that said Letters Patent is hereby corrected as shown below:

On the Title page, Item [75] should read:

Inventors: Ashok K. Raina, Beltsville; Howard Jaffe, Gaithersburg; Tomas G. Kempe, Bowie, all of MD.

Signed and Sealed this

Twenty-ninth Day of March, 1994

Attest:

BRUCE LEHMAN

Attesting Officer    Commissioner of Patents and Trademarks